(12) United States Patent
Bullington

(10) Patent No.: US 6,562,843 B1
(45) Date of Patent: May 13, 2003

(54) SUBSTITUTED 3-PYRIDYL-4-ARYLPYRROLES, AND RELATED THERAPEUTIC AND PROPHYLACTIC METHODS

(75) Inventor: James L. Bullington, Hamilton Square, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/561,534

(22) Filed: Apr. 28, 2000

Related U.S. Application Data

(60) Provisional application No. 60/134,139, filed on May 14, 1999.

(51) Int. Cl.$^7$ .................. A61K 31/4439; A61K 31/496; C07D 401/04; C07D 401/14
(52) U.S. Cl. .................. 514/340; 514/459; 546/276.4; 544/124; 544/106; 544/111; 544/114
(58) Field of Search .................. 546/276.4; 544/124, 544/111, 114, 106; 514/340, 459

(56) References Cited

U.S. PATENT DOCUMENTS 5,776,954 A    7/1998    de Laszlo et al.

FOREIGN PATENT DOCUMENTS

| EP | 0254241 A1 | 1/1988 |
| GB | 1489280 | 10/1977 |
| WO | WO93/14081 | 7/1993 |
| WO | WO97/05878 | 2/1997 |
| WO | WO 97/16442 A | 5/1997 |
| WO | 97/16442 * | 9/1997 |
| WO | WO 98/02430 A | 2/1998 |

OTHER PUBLICATIONS

M. Chahma et al, J. Org. Chem 1995, vol. 60 pp. 8015–8022. Jul. 1995.*
PCT International Search Report—Application No. PCT/US01/25289 dated Mar. 21, 2002.
D. Griswold, et al., Pharmacology of Cytokine Suppressive Anti–Inflammatory Drug Binding Protein (CSBP), A Novel Stress–Induced Kinase, *Pharmacology Communications*, 1996, 7, 323–29.
Davis, Roger J., et al., Opposing effects of ERK and JNK–p38 MAP Kinases on Apoptosis, *Science*, 1995, 270 (5240), 1326–31.
Heidenreich, Kim A., et al., Inhibition of p38 Mitogen–Activated Protein Kinase by Insulin in Cultured Fetal Neurons, *J. Biol. Chem.*, 1996, 271 (17), 9891–4.
Arvanitakis, L., et al., G–Protein–Coupled Receptor of Kaposi's Sarcoma–Associated Herpesvirus is a Viral Oncogene and Angiogenesis Activator, *Nature*, 1998, 391 (6662), 86–89.
Pitha, Paula M., et al., Early Activation of Mitogen–Activated Protein Kinase Kinase, Extracellular Signal–Regulated Kinase, p38 Mitogen–Activated Protein Kinase, and c–Jun N–terminal Kinase in Response to Binding of Simian Immunodeficiency Virus to Jurkat T Cells Expressing CCR5 Receptor, *Virology*, 1998, 252 (1), 210–217.
Bukrinsky, M., The Critical Role of p38 MAP Kinase in T Cell HIV–1 Replication, *Mol. Med.*, 1997, 3 (5), 339–346.
C. Dinarello, et al., Inflammatory Cytokines: Interleukin–1 and Tumor Necrosis Factor as Effector Molecules in Autoimmune Diseases, *Curr. Opin. Immunol.* 1991, 3, 941–48.
M. J. Elliot, et al., Treatment of Rheumatoid Arthritis with Chimeric Monoclonal Antibodies to Tumor Necrosis Factor α, *Arthritis Rheum.*, 1993, 36, 1681–90.
J. C. Boehm, et al., 1–Substituted 4–Aryl–5–pyridinylimidazoles: A New Class of Cytokine Suppressive Drugs with Low 5–Lipoxygenase and Cyclooxygenase Inhibitory Potency, *J. Med. Chem.*, 1996, 39, 3929–37.
A. M. Badger, et al., Pharmacological Profile of SB 203580, A Selective Inhibitor of Cytokine Suppressive Binding Protein p38 Kinase, in Animal Models of Arthritis, Bone Resorption, Endotoxin Shock and Immune Function, *The Journal of Pharmacology and Experimental Therapeutics*, 1996, 279, 1453–61.
English Abstract –XP–002193795 –S. Andronati et al.— Pharmazie, vol. 54, No. 2, pp. 99–101 (1999) –Chemical Abstracts Sevice, Columbus, Ohio.
Japanese Abstract –XP–022193796 –JP52014765 A—Chemical Abstract Service, Columbus, Ohio.
Japanese Abstract –XP–002193797 –JP50116470 A—Chemical Abstract Service, Columbus, Ohio.
Japanese Abstract –XP–002193692 –WO98/56785 A—Chemical Abstract Service, Columbus, Ohio.

* cited by examiner

Primary Examiner—Alan L. Rotman
Assistant Examiner—Rita Desai

(57) ABSTRACT

This invention provides novel substituted 3-pyridyl-4-arylpyrroles, and pharmaceutical compositions comprising same, useful for treating disorders ameliorated by reducing TNF-α production and/or p38 activity in appropriate cells. This invention also provides therapeutic and prophylactic methods using the instant pharmaceutical compositions.

19 Claims, No Drawings

SUBSTITUTED 3-PYRIDYL-4-ARYLPYRROLES, AND RELATED THERAPEUTIC AND PROPHYLACTIC METHODS

This application claims the benefit under 35 U.S.C. §119(e) of prior application Ser. No. 60/134,139, filed May 14, 1999, which is incorporated herein by reference.

FIELD OF THE INVENTION

This invention relates to novel substituted 3-pyridyl-4-arylpyrroles and their therapeutic and prophylactic uses. Disorders treated and/or prevented using these compounds include inflammatory and AIDS-related disorders.

BACKGROUND OF THE INVENTION

TNF-α and p38-Related Disorders

Inflammatory cytokines such as TNF-α are produced via the activity of kinases. Such kinases include the Cytokine Suppressive Antiinflammatory Drug-Binding Protein (CSBP)/p38 kinase, a Mitogen-Activated Protein (MAP) kinase family of serine-threonine protein kinases. Inflammatory cytokines play an important role in a number of inflammatory disorders (1), neurodegenerative disorders (10), and AIDS-related disorders (11–14). Although the precise mechanism of kinases such as p38 is unknown, p38 has been implicated in both the production of TNF-α and the signaling responses associated with the TNF-α receptor (6).

Arthritis is a prime example of an inflammatory disorder, and is thus the inflammatory disorder focused on most in this section. Arthritis affects millions of people and can strike at any joint in the human body. Its symptoms range from mild pain and inflammation in affected joints, to severe and debilitating pain and inflammation. Although the disorder is associated mainly with aging adults, it is not restricted to adults.

The most common rheumatoid arthritis therapy involves the use of nonsteroidal anti-inflammatory drugs (NSAID's) to alleviate symptoms.

However, despite the widespread use of NSAID's, many individuals cannot tolerate the doses necessary to treat the disorder over a prolonged period of time. In addition, NSAID's merely treat the symptoms of disorder without affecting the underlying cause.

Other drugs such as methotrexate, gold salts, D-penicillamine and prednisone are often used when patients fail to respond to NSAID's. These drugs also have significant toxicities and their mechanism of action remains unknown. Monoclonal antibodies to TNF-α and receptor antagonists to interleukin 1β (IL-1β) have been shown to reduce symptoms of rheumatoid arthritis in small-scale human clinical trials (2).

In addition to protein-based therapies, there are small molecule agents that inhibit the production of these cytokines and have demonstrated activity in animal rheumatoid arthritis models (3). Of these small molecule agents, SB 203580 has proven effective in reducing the production of TNF-α and IL-1β in lipopolysaccharide (LPS)-stimulated human monocyte cell lines with $IC_{50}$ values of 50 to 100 nM (4).

In addition to in vitro testing results, SB 203580 has been shown to inhibit the production of inflammatory cytokines in rats and mice at $IC_{50}$ values of 15 to 25 mg/kg (5). SB 203580 reduces the production of inflammatory cytokines by inhibiting the activity of CSBP/p38 kinase at an $IC_{50}$ of 200 nM (6). Due to SB 203580's oral activity and potency in animal models, researchers have suggested that a compound with such an activity profile has potential as a viable treatment for rheumatoid arthritis (5).

Pyridylpyrroles and their analogs have also been prepared as cytokine inhibitors and glucagon antagonists (7), and specifically as inhibitors of IL-1β, TNF-α and other cytokines. Arylpyrroles (8) and triarylpyrroles (9) have also been prepared as cytokine inhibitors.

The role of CSBP/p38 has been implicated recently in various neurodegenerative and AIDS-related disorders. With regard to neurodegenerative disorders, p38 has been shown to have a role in determining whether a cell survives or undergoes neuronal programmed cell death or apoptosis (10, 11).

Also related to AIDS, the Kaposi's sarcoma-associated herpesvirus HHV8 has been shown to encode a G protein-coupled receptor that activates p38. It has been proposed that this activation contributes to tumorigenesis and angiogenesis leading to Kaposi's sarcoma (12).

Associated with AIDS is the rapid activation of p38 induced by infection of a $CCR5^+$ human T cell line by SIV, suggesting that p38 may play a role in early viral infection (13). Additionally, p38 inhibitors have been shown to block HIV replication in vitro in a manner that may be TNF-α-independent (14).

Absence of Clinically Effective Agents

In general, arthritis—particularly rheumatoid arthritis—and the host of other inflammatory and AIDS-related disorders all take a severe toll on those afflicted. There is a tremendous need for small molecule agents to treat these disorders. To date, however, no such agents have ever been identified and shown to be clinically effective in humans.

SUMMARY OF THE INVENTION

This invention provides a compound having the structure:

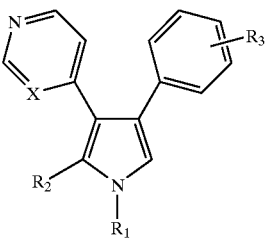

or a pharmaceutically acceptable salt thereof, wherein:
(a) $R_1$ is selected from the group consisting of (i) hydrogen, (ii) $C_{1-5}$alkyl, (iii) substituted or unsubstituted $C_{1-5}$alkylamino, (iv) N-containing $C_{1-5}$alkyl heterocycle selected from thiazolidine, piperidine, morpholine, piperazine, thiomorpholine, pyrrolidine, thiazine, pyrrole and imidazole, (v) phenyl, (vi) phenyl independently substituted with one or more of $C_{1-5}$alkyl, amino, substituted amino, nitro, nitrile and sulfone, and (vii) pyridine;
(b) $R_2$ is selected from the group consisting of (i) hydrogen, (ii) $(CH_2)_3OH$, (iii) substituted or unsubstituted C$_{1-5}$alkyl phenyl, and (iv) N-containing C$_{1-5}$alkyl heterocycle selected from thiazolidine, piperidine, morpholine, piperazine, thiomorpholine, pyrrolidine, thiazine, pyrrole and imidazole;

(c) R$_3$ is one or more substituents independently selected from the group consisting of hydrogen, halogen, methoxy, nitro, trifluoromethyl, hydroxy, dimethylamino and methylsulfoxide; and (d) X is either C or N.

This invention also provides a second compound having the structure:

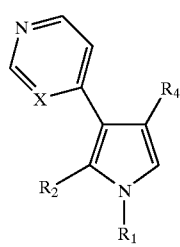

or a pharmaceutically acceptable salt thereof, wherein:

(a) R$_1$ is selected from the group consisting of (i) hydrogen, (ii) C$_{1-5}$alkyl, (iii) substituted or unsubstituted C$_{1-5}$alkylamino, (iv) N-containing C$_{1-5}$alkyl heterocycle selected from thiazolidine, piperidine, morpholine, piperazine, thiomorpholine, pyrrolidine, thiazine, pyrrole and imidazole, (v) phenyl, (vi) phenyl independently substituted with one or more of C$_{1-5}$alkyl, amino, substituted amino, nitro, nitrile and sulfone, and (vii) pyridine;

(b) R$_2$ is selected from the group consisting of (i) hydrogen, (ii) (CH$_2$)$_3$OH, (iii) substituted or unsubstituted C$_{1-5}$alkyl phenyl, and (iv) N-containing C$_{1-5}$alkyl heterocycle selected from thiazolidine, piperidine, morpholine, piperazine, thiomorpholine, pyrrolidine, thiazine, pyrrole and imidazole;

(c) R$_4$ is a substituted or unsubstituted heterocycle selected from pyridine, pyrimidine, furan or thiophene; and, (d) X is either C or N.

This invention further provides a pharmaceutical composition comprising one of the instant compounds and a pharmaceutically acceptable carrier.

This invention still further provides a method of treating a subject having a disorder ameliorated by reducing TNF-α production and/or p38 activity in appropriate cells, which comprises administering to the subject a therapeutically effective dose of the instant pharmaceutical composition.

Finally, this invention provides a method of preventing an inflammatory response in a subject, comprising administering to the subject a prophylactically effective amount of the instant pharmaceutical composition either preceding or subsequent to an event anticipated to cause the inflammatory response in the subject.

DETAILED DESCRIPTION OF THE INVENTION

This invention provides novel substituted 3-pyridyl-4-arylpyrroles. These compounds have surprising usefulness in treating disorders ameliorated by a reduction in TNF-α production and/or p38 activity, and are therefore useful for treating inflammatory disorders such as rheumatoid arthritis, as well as AIDS-related disorders.

Specifically, this invention provides a first compound having the structure:

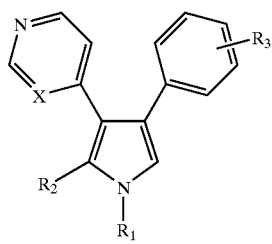

or a pharmaceutically acceptable salt thereof, wherein:

(a) R$_1$ is selected from the group consisting of (i) hydrogen, (ii) C$_{1-5}$alkyl, (iii) substituted or unsubstituted C$_{1-5}$alkylamino, (iv) N-containing C$_{1-5}$alkyl heterocycle selected from thiazolidine, piperidine, morpholine, piperazine, thiomorpholine, pyrrolidine, thiazine, pyrrole and imidazole, (v) phenyl, (vi) phenyl independently substituted with one or more of C$_{1-5}$alkyl, amino, substituted amino, nitro, nitrile and sulfone, and (vii) pyridine;

(b) R$_2$ is selected from the group consisting of (i) hydrogen, (ii) (CH$_2$)$_3$OH, (iii) substituted or unsubstituted C$_{1-5}$alkyl phenyl, and (iv) N-containing C$_{1-5}$alkyl heterocycle selected from thiazolidine, piperidine, morpholine, piperazine, thiomorpholine, pyrrolidine, thiazine, pyrrole and imidazole;

(c) R$_3$ is one or more substituents independently selected from the group consisting of hydrogen, halogen, methoxy, nitro, trifluoromethyl, hydroxy, dimethylamino and methylsulfoxide; and (d) X is either C or N.

In one embodiment of the first compound:

(a) R$_1$ is selected from the group consisting of (i) hydrogen, (ii) C$_{1-5}$alkyl, (iii) substituted or unsubstituted C$_{1-5}$alkylamino, (iv) N-containing C$_{1-5}$alkyl heterocycle selected from piperidine, morpholine and pyrrolidine, and (v) phenyl substituted with a substituent selected from the group consisting of amino, substituted amino, nitro and nitrile;

(b) R$_2$ is selected from the group consisting of hydrogen and (CH$_2$)$_3$phenyl;

(c) R$_3$ is selected from the group consisting of halogen, nitro and trifluoromethyl; and (d) X is C.

In the preferred embodiment, the first compound is selected from the group of compounds shown in Table 1.

TABLE 1
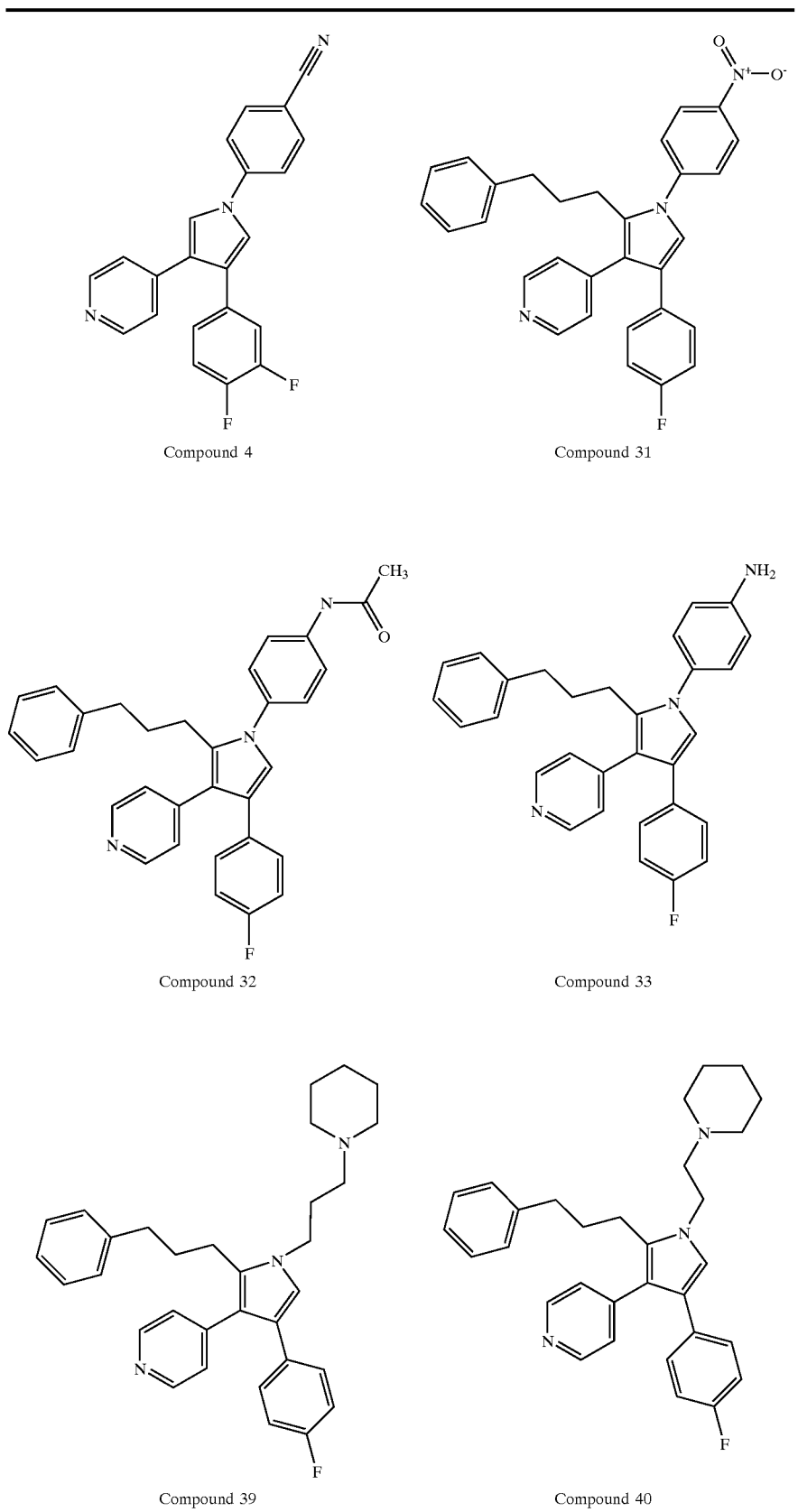

TABLE 1-continued
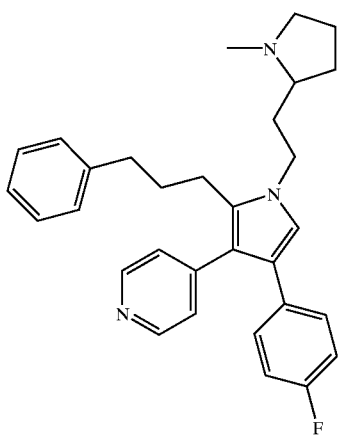
Compound 41
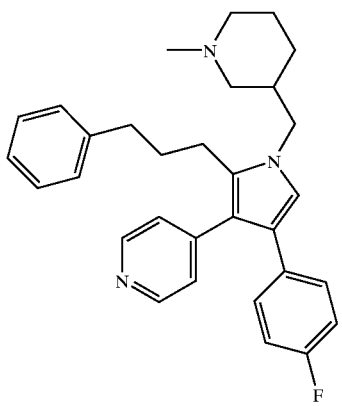
Compound 42
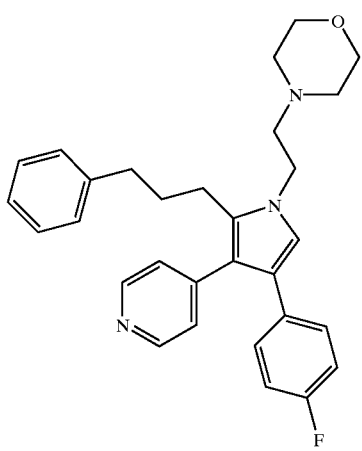
Compound 43
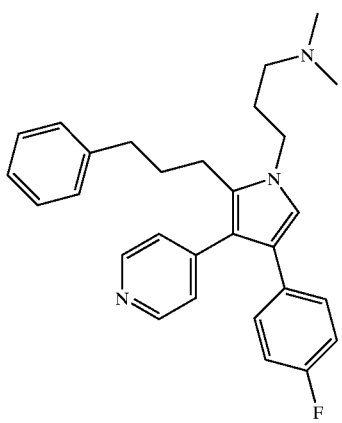
Compound 44
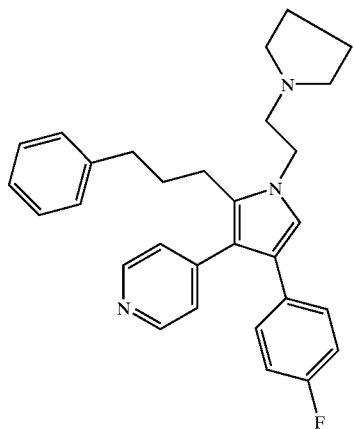
Compound 45
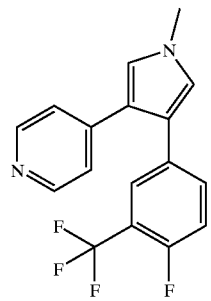
Compound 7

TABLE 1-continued

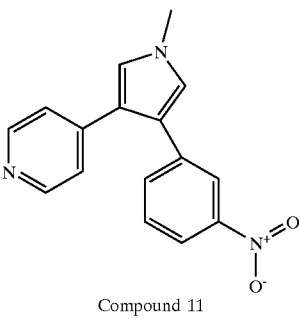

Compound 11

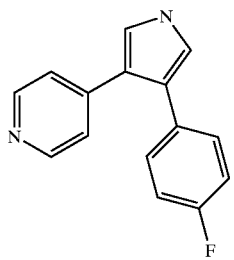

Compound 27

This invention also provides a second compound having the structure:

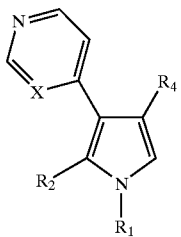

or a pharmaceutically acceptable salt thereof, wherein:

(a) $R_1$ is selected from the group consisting of (i) hydrogen, (ii) $C_{1-5}$alkyl, (iii) substituted or unsubstituted $C_{1-5}$alkylamino, (iv) N-containing $C_{1-5}$alkyl heterocycle selected from thiazolidine, piperidine, morpholine, piperazine, thiomorpholine, pyrrolidine, thiazine, pyrrole and imidazole, (v) phenyl, (vi) phenyl independently substituted with one or more of $C_{1-5}$alkyl, amino, substituted amino, nitro, nitrile and sulfone, and (vii) pyridine;

(b) $R_2$ is selected from the group consisting of (i) hydrogen, (ii) $(CH_2)_3OH$, (iii) substituted or unsubstituted $C_{1-5}$alkyl phenyl, and (iv) N-containing $C_{1-5}$alkyl heterocycle selected from thiazolidine, piperidine, morpholine, piperazine, thiomorpholine, pyrrolidine, thiazine, pyrrole and imidazole;

(c) $R_4$ is a substituted or unsubstituted heterocycle selected from pyridine, pyrimidine, furan or thiophene; and, (d) X is either C or N.

In one embodiment of the second compound:

(a) $R_1$ is selected from the group consisting of (i) $C_{1-5}$alkyl, (ii) substituted or unsubstituted $C_{1-5}$alkylamino, (iii) substituted or unsubstituted $C_{1-5}$alkyl heterocyclic amino, (iv) phenyl, and (v) phenyl independently substituted with one or more of amino, substituted amino, nitro or nitrile;

(b) $R_2$ is selected from the group consisting of hydrogen and $(CH_2)_3$phenyl; and (c) X is C.

The instant compounds can be isolated and used as free bases. They can also be isolated and used as pharmaceutically acceptable salts. Examples of such salts include hydrobromic, hydroiodic, hydrochloric, perchloric, sulfuric, maleic, fumaric, malic, tartaric, citric, benzoic, mandelic, methanesulfonic, hydroethanesulfonic, benzenesulfonic, oxalic, palmoic, 2-naphthalenesulfonic, p-toluenesulfonic, cyclohexanesulfamic and saccharic.

This invention further provides a pharmaceutical composition comprising one of the instant compounds and a pharmaceutically acceptable carrier.

Pharmaceutically acceptable carriers are well known to those skilled in the art and include, but are not limited to, from about 0.01 to about 0.1 M and preferably 0.05 M phosphate buffer or 0.8% saline. Such pharmaceutically acceptable carriers can be aqueous or non-aqueous solutions, suspensions and emulsions. Examples of non-aqueous solvents are propylene glycol, polyethylene glycol, vegetable oils such as olive oil, and injectable organic esters such as ethyl oleate. Aqueous carriers include water, ethanol, alcoholic/aqueous solutions, glycerol, emulsions or suspensions, including saline and buffered media. Oral carriers can be elixirs, syrups, capsules, tablets and the like. The typical solid carrier is an inert substance such as lactose, starch, glucose, methyl-cellulose, magnesium stearate, dicalcium phosphate, mannitol and the like. Parenteral carriers include sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention still further provides a method of treating a subject having a disorder ameliorated by reducing TNF-α production and/or p38 activity in appropriate cells, which comprises administering to the subject a therapeutically effective dose of the instant pharmaceutical composition.

In one embodiment, the disorder is an inflammatory disorder. In another embodiment, the disorder is an AIDS-related disorder. Examples of disorders treatable by the instant pharmaceutical composition include, without limitation, rheumatoid arthritis, osteoporosis, osteoarthritis, allergic inflammation, periodontal disorder, inflammatory bowel disorder, septic shock, insulin-dependent diabetes mellitus, non-insulin-dependent diabetes, cachexia, pulmonary fibrosis, myasthenia gravis, Crohn's disease, hepatitis, primary biliary cirrhosis, acute pancreatitis, allograph rejection, glioblastoma, alopecia areta, psoriasis, ischemia, congestive heart failure, restenosis, atherosclerosis, systemic lupus erythematosus, nephritis, Guillain-Barre Syndrome, viral myocarditis, HIV replication, T-cell depletion in HIV infection, cognitive deficits induced by neuronal inflammation, multiple sclerosis, stroke, neuropathic pain, HIV dementia and Alzheimer's disease. In the preferred embodiment, the disorder is rheumatoid arthritis.

As used herein, the term "subject" includes, without limitation, any animal or artificially modified animal having a disorder ameliorated by reducing TNF-α production and/or p38 activity in appropriate cells. In the preferred embodiment, the subject is a human.

As used herein, "appropriate cells" include, by way of example, cells which secrete or are capable of secreting TNF-α, and cells wherein p38 has been activated. Specific examples of appropriate cells include, without limitation, monocytes, macrophages, T lymphocytes, fibroblasts, dendritic cells, Langerhans cells, Kuppfer cells and astroglial cells.

Administering the instant pharmaceutical composition can be effected or performed using any of the various methods known to those skilled in the art. The instant compounds can be administered, for example, intravenously, intramuscularly, orally and subcutaneously. In the preferred embodiment, the instant pharmaceutical composition is administered orally. Additionally, administration can comprise giving the subject a plurality of dosages over a suitable period of time. Such administration regimens can be determined according to routine methods.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

In one embodiment, the therapeutically and/or prophylactically effective dose is a dose sufficient to deliver from about 0.05 mg/kg of body weight to about 200 mg/kg of body weight of the instant pharmaceutical composition. In another embodiment, the therapeutically and/or prophylactically effective dose is a dose sufficient to deliver from about 0.5 mg/kg of body weight to about 50 mg/kg of body weight. More specifically, in one embodiment, oral doses range from about 0.05 mg/kg to about 100 mg/kg daily. In another embodiment, oral doses range from about 0.05 mg/kg to about 50 mg/kg daily, and in a further embodiment, from about 0.05 mg/kg to about 20 mg/kg daily. In yet another embodiment, infusion doses range from about 1.0 μg/kg/min to about $1.0 \times 10^4$ μg/kg/min of inhibitor, admixed with a pharmaceutical carrier over a period ranging from about several minutes to about several days. In a further embodiment, for topical administration, the instant compound can be combined with a pharmaceutical carrier at a drug/carrier ratio of from about 0.001 to about 0.1.

This invention still further provides a method of preventing an inflammatory response in a subject, comprising administering to the subject a prophylactically effective amount of the instant pharmaceutical composition either preceding or subsequent to an event anticipated to cause the inflammatory response in the subject. In the preferred embodiment, the event is an insect sting or an animal bite.

As used herein, the following chemical terms shall have the meanings as set forth in this paragraph: "independently", when in reference to chemical substituents, shall mean that when more than one substituent exists, the substituents may be the same or different; "alkyl" shall mean straight, cyclic and branched-chain alkyl; "alkoxy" shall mean O-alkyl; "halogen" shall mean fluorine, chlorine, bromine or iodine; "Ph" shall mean phenyl; "TCA" shall mean trichloroacetic acid; "FCS" shall mean fetal calf serum; and "RPMI" shall mean the medium from the Roswell Park Memorial Institute (Sigma cat # R0833).

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

EXPERIMENTAL DETAILS

I. General Synthetic Schemes

Representative compounds of the present invention can be synthesized in accordance with the general synthetic methods described below and illustrated in the following general schemes. The products of some schemes can be used as intermediates to produce more than one of the instant compounds. In those cases, the choice of intermediates to be used to produce subsequent compounds of the present invention is a matter of discretion that is well within the capabilities of those skilled in the art.

Scheme 1

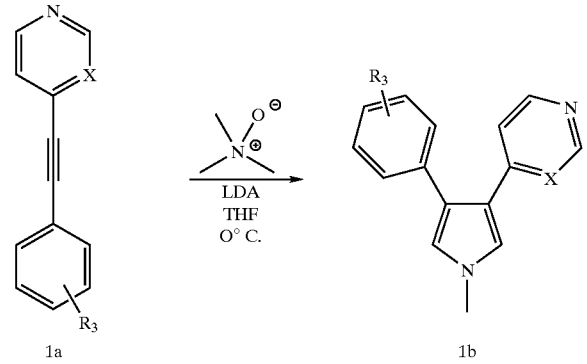

Scheme 1 can be used to produce the compounds of the invention where $R_1$ is methyl. Compound 1a, such as a 1,2-disubstituted alkyne, can be used as the starting material for Scheme 1. 1,2-disubstituted alkynes can be prepared following known procedures. The substituents X and $R_3$ of the compounds of the invention are determined by the substituents of Compound 1a. Compound 1a is combined with trimethylamine-N-oxide and dissolved in a dry solvent, such as THF, and cooled to 0° C. A base, such as lithium diisopropylamide, is added and the reaction is stirred at 0° C. for 1 h to give Compound 1b as the product.

Scheme 2

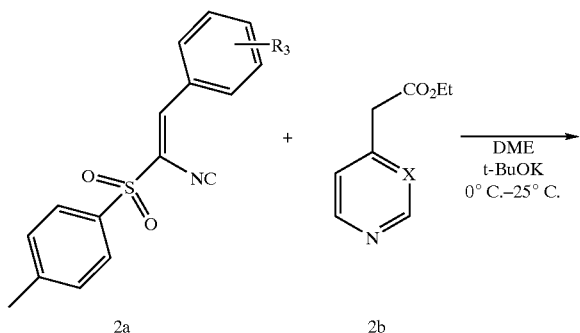

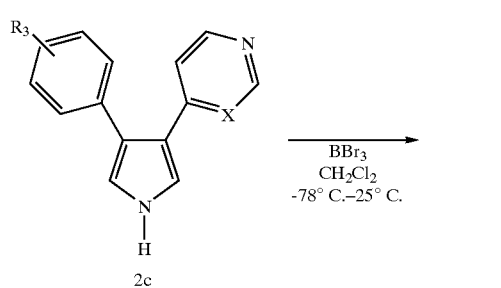

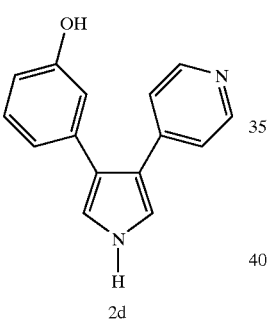

Scheme 3

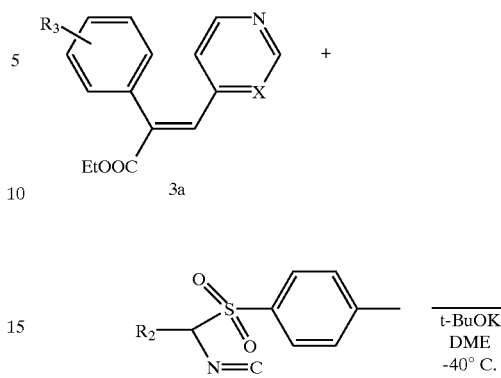

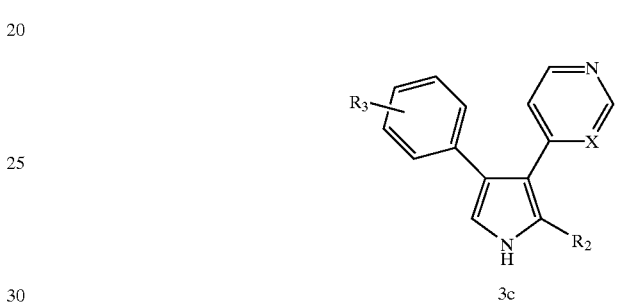

Scheme 2 can be used to prepare compounds of the invention where $R_1$ is hydrogen. Compound 2a, of the type 1-[(1-isocyano-2-(3-methoxy-phenyl)ethenyl)sulfonyl]-4-methylbenzene can be used as the starting material for Scheme 2. Compound 2a can be prepared following known procedures. The substituent $R_3$ of the compounds of the invention are generally determined by the substituents on the phenyl of the ethynyl group in Compound 2a; the X atom is determined by the heteroaromatic substituent of the acetate group in Compound 2b. Compound 2a is dissolved in a dry solvent, such as ethylene glycol dimethyl ether, and added dropwise to a mixture of Compound 2b, such as ethyl 4-pyridylacetate, and a base, such as potassium t-butoxide, in a dry solvent, such as ethylene glycol dimethyl ether, at 0° C. After the addition is complete, the reaction is warmed to 25° C. and stirred for 3 h to give the intermediate Compound 2c. When $R_3$ is methoxy, the intermediate Compound 2c can be treated with a demethylating agent, such as $BBr_3$, in an inert solvent, such as $CH_2CL_2$, at −78° C. to give Compound 2d.

Scheme 3 can be used to produce the compounds of the invention where $R_1$ is hydrogen and $R_2$ is substituted or unsubstituted. Compound 3a, a diaryl substituted α,β-unsaturated ester, can be used as the starting material for Scheme 3. Compounds of this type can be prepared following known procedures. Compound 3b can be the other starting material, a substituted tosylmethyl isocyanide (tosMIC) derivative that can be prepared following known procedures.

For example, Compound 3a can be ethyl 4-fluoro-α-[(4-pyridyl)methylene]benzeneacetic acid and Compound 3b can be 1-(4-tolylsulfonyl)-1-(3-phenylpropyl)methyl isocyanide. Compound 3a and Compound 3b are dissolved in dry solvent, such as ethylene glycol dimethyl ether, and added dropwise to a −40° C. mixture of a base, such as potassium t-butoxide, in a dry solvent, such as ethylene glycol dimethyl ether. Stirring at −40° C. is continued for 1 hour before allowing the temperature to rise to −20° C. Accordingly, the resulting Compound 3c is 4-(4-fluorophenyl)-2-(3-phenylpropyl)-3-(4-pyridyl)pyrrole (Compound 27).

As shown in Scheme 4, Compound 2c and Compound 3c can be used as intermediates to form other compounds of the present invention.

Scheme 4

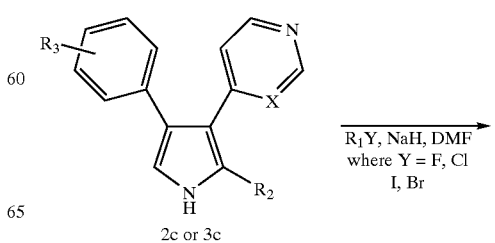

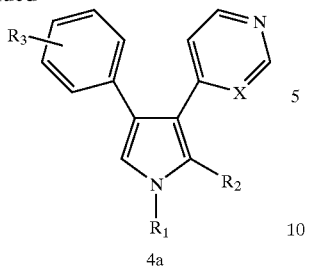

4a

Scheme 4 can be used to produce the compounds of the invention where $R_1$ is substituted. Intermediate Compound 2c or Compound 3c is added portionwise to a base, such as sodium hydride, in a solvent, such as dimethylformamide, at 0° C. After the addition is complete, the reaction is stirred at 0° C. an additional 15 minutes followed by portionwise addition of an alkylating agent, such as 4-(2-chloroethyl) morpholine hydrochloride. The reaction is heated to 60° C. for 16 hours before the temperature is allowed to cool to 25° C. to produce Compound 4a.

Scheme 5

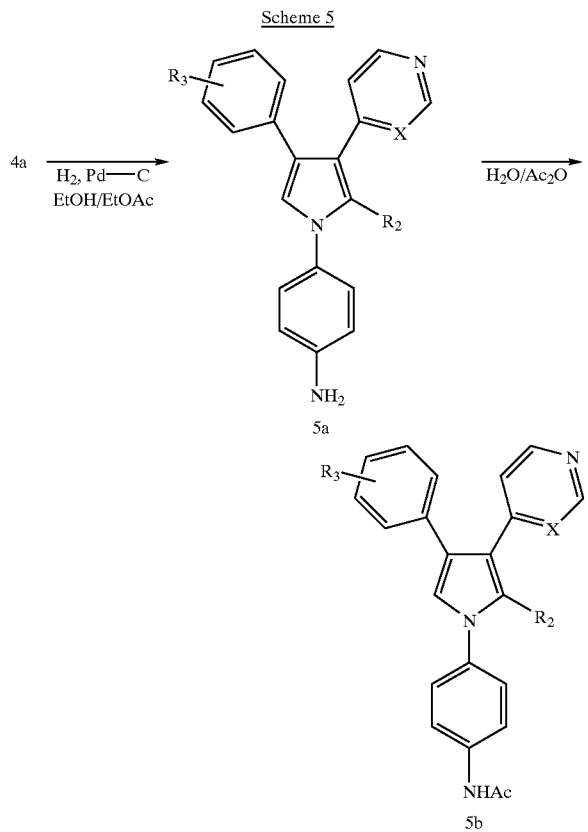

Scheme 5 can be used to produce the compounds of the invention where $R_1$ is substituted. When $R_1$ is 4-nitrophenyl, the intermediate Compound 4a can be reduced using a catalyst, such as palladium on carbon in a solvent, such as ethyl acetate, to give Compound 5a. The amine Compound 5a can be treated with an acylating agent, such as acetic anhydride, in a solvent, such as water, to give the product Compound 5b.

Scheme 6

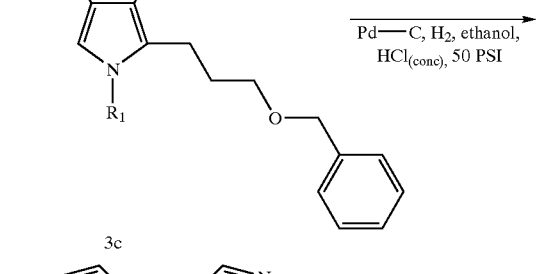
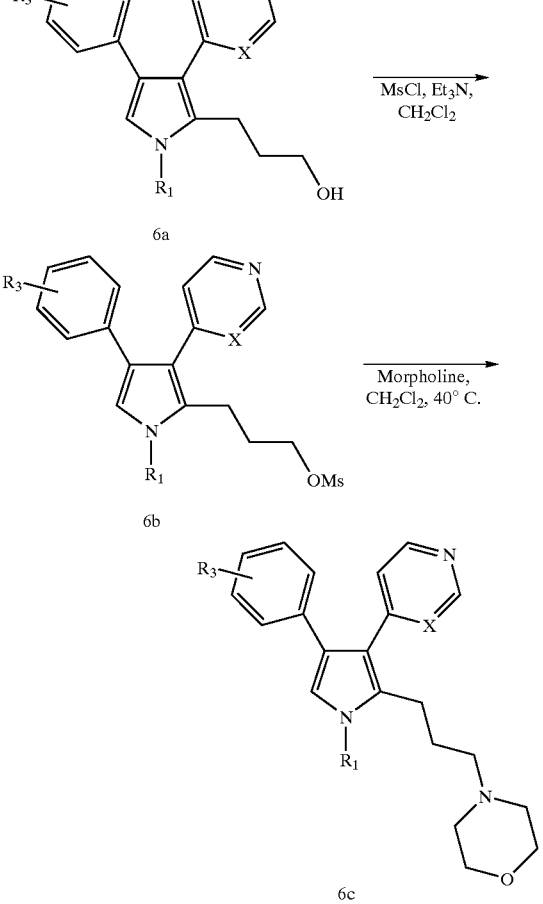

Scheme 6 can be used to produce the compounds of the invention where $R_2$ is an alkyl chain containing heteroatoms. Intermediate Compound 3c is exposed to reducing conditions using a catalyst, such as palladium on carbon in a solvent, such as ethanol, to which a catalytic amount of acid, such as concentrated hydrochloric acid, is added to give Compound 6a. The alcohol Compound 6a can be treated with an sulfonating agent, such as mesyl chloride, and a base, such as triethylamine, in a solvent, such as $CH_2Cl_2$, to give the intermediate Compound 6b. Compound 6b can then be heated with a nucleophile, such as morpholine, in a solvent, such as $CH_2Cl_2$, to give Compound 6c.

II. Specific Compound Syntheses

Specific compounds which are representative of this invention can be prepared as per the following examples. No attempt has been made to optimize the yields obtained in these reactions. Based on the following, however, one skilled in the art would know how to increase yields through routine variations in reaction times, temperatures, solvents and/or reagents.

The products of certain syntheses can be used as intermediates to produce more than one of the instant compounds. In those cases, the choice of intermediates to be used to produce compounds of the present invention is a matter of discretion that is well within the capabilities of those skilled in the art.

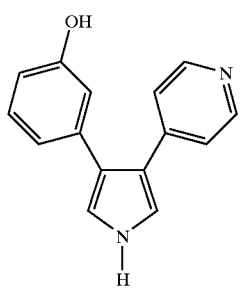

Compound 12

3-(3-Hydroxyphenyl)-4-(4-pyridyl)pyrrole Hydrobromide

Compound 13 (0.15 g, 0.006 mol) was dissolved in CH$_2$Cl$_2$ (50 mL) and cooled to −78° C. The mixture was stirred for 16 h, allowing the temperature to warm to 25° C. The reaction was quenched with MeOH (20 mL) and evaporated to a solid. The solid was triturated with ether and filtered to give Compound 12 (0.15 g, 79% yield). $^1$HNMR (DMSO-d6) δ 11.91 (1H, s, NH), 9.47 (1H, br s, OH), 8.66 (2H, d, J=8.6), 7.86–7.86 (3H, m), 7.25–7.14 (1H, m) 7.06 (1H, s) 6.80–6.66 (3H, m).

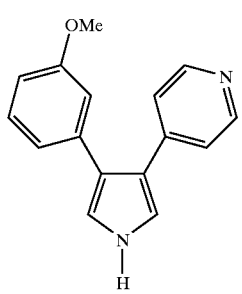

Compound 13

3-(3-Methoxyphenyl)-4-(4-pyridyl)pyrrole

1-[(1-isocyano-2-(3-methoxyphenyl)ethenyl)sulfonyl]-4-methylbenzene (9.0 g, 0.0285 mol) was dissolved in dry DME (200 mL) and added dropwise to a cooled (0° C.) mixture of ethyl 4-pyridylacetate (9.0 g, 0.545 mol) and potassium t-butoxide (7.1 g, 0.0633 mol) in dry DME (100 mL). After the addition was complete the reaction was warmed to 25° C. and stirred for 3 h. The reaction was then poured into ice water (1200 mL) and extracted into CH$_2$Cl$_2$ (3×500 mL). The combined organics were dried over Na$_2$SO$_4$, filtered and evaporated in vacuo to give a solid. This solid was then triturated with ether and filtered to give 3.0 g of pure 3-(3-methoxyphenyl)-4-(4-pyridyl)pyrrole. The filtrate was again evaporated in vacuo and then triturated with a 50/50 mixture of CH$_2$Cl$_2$ and ether to give an additional 1.5 g of pure product. Finally the filtrate was evaporated in vacuo and purified on SiO$_2$ eluting with ethyl acetate to give another 0.5 g of pure product resulting in a 70% combined yield. $^1$HNMR (DMSO-d6) δ 11.38 (1H, br s, NH), 8.37 (2H, d, J=6.1), 7.24–7.17 (4H, m), 7.02–7.00 (1H, m), 6.80–6.77 (3H, m), 3.68 (3H, s).

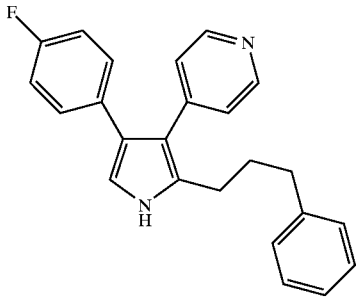

Compound 27

4-(4-Fluorophenyl)-2-(3-phenylpropyl)-3-(4-pyridyl) pyrrole 1-(4-tolylsulfonyl)-1-(3-phenylpropyl)methyl isocyanide (10.9 g, 0.0346 mol) and ethyl 4-fluoro-α-[(4-pyridyl) methylene]benzeneacetic acid (9.4 g, 0.0346 mol) were dissolved in dry DME (250 mL) and added dropwise to a cooled (40° C.) mixture of potassium t-butoxide (9.5 g, 0.0847 mol) in dry DME (50 mL). The mixture was stirred for 1 hour allowing the temperature to rise to −20° C. The mixture was poured into H$_2$O (1800 mL) and extracted into CH$_2$Cl$_2$ (3×500 mL). The combined organics were dried over Na$_2$SO$_4$ and evaporated in vacuo to give a solid. Trituration of the solid with acetonitrile gave pure Compound 27 (6.0 g, 49% yield). $^1$HNMR (DMSO-d6) δ 11.17 (1H, s, NH), 8.38 (2H, d, J=5.8 Hz), 7.27–6.92 (12H, m), 2.61–2.51 (4H, m), 1.93–1.83 (2H, m).

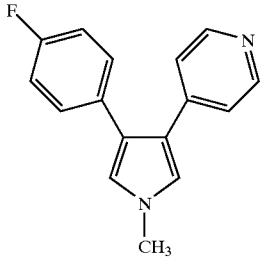

Compound 28

1-Methyl-3-(4-fluorophenyl)-4-(4-pyridyl)pyrrole

4-[(4-fluorophenyl)ethynyl]pyridine (2.0 g, 0.0101 mol) and trimethylamine-N-oxide (1.0 g, 0.0133 mol) were dissolved in dry THF (200 mL) and cooled to 0° C. Lithium diisopropylamide (1.5M in THF, 14 mL) was added and the reaction was stirred at 0° C. for 1 h. The reaction was then quenched with H$_2$O (20 mL) and extracted into CH$_2$Cl$_2$ (2×100 mL). The organics were dried over Na$_2$SO$_4$ and evaporated in vacuo to give an oil. Purification on SiO$_2$ eluting with EtOAc gave 0.356 g (14% yield) of Compound 28. $^1$HNMR (CDCl$_3$) δ 8.41 (2H, d, J=5.4 Hz), 7.19 (2H, dd, J=5.7, 6.0 Hz), 7.11 (2H, d, J=5.4 Hz), 6.99 (2H, dd, J=8.7, 8.5 Hz), 6.87 (1H, d, J=2.1 Hz), 6.69 (1H, d, J=2.4 Hz), 3.71 (3H, s).

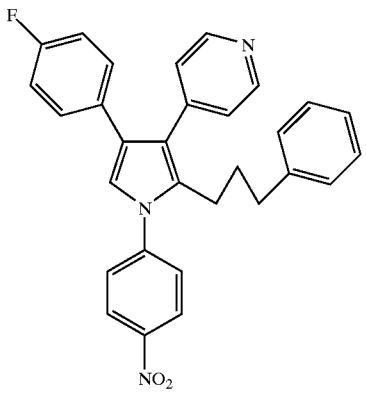

Compound 30

4-(4-Fluorophenyl)-1-(4-nitrophenyl)-2-(3-phenylpropyl)-3-(4-pyridyl)pyrrole

Sodium hydride (60% in mineral oil, 0.80 g, 0.0209 mol) was washed 3 times with hexane and then dissolved in DMF (15 mL). Compound 27 (6.0 g, 0.01683 mol) was then added portionwise at 0° C. with stirring. After the addition was complete, the reaction was stirred at 0° C. an additional 15 minutes followed by dropwise addition of 4-fluoronitrobenzene (2.4 g, 0.170 mol). The reaction was stirred at 0° C. for 1 h before the temperature was allowed to warm to 25° C. The reaction was poured into 1.5 L of water and extracted into $CH_2Cl_2$ (3×500 mL). The combined organics were washed with water (4×500 mL) and dried over $Na_2SO_4$. Evaporation in vacuo gave a yellow solid which was triturated with acetonitrile, filtered and air dried to give 6.6 g (82.5% yield) of pure Compound 30. $^1$HNMR (CDCl$_3$) δ 8.52 (2H, d, J=5.8 Hz), 8.26 (2H, d, J=8.9 Hz), 7.46 (2H, d, J=8.9 Hz), 7.16–7.13 (3H, m), 7.09–7.03 (4H, m), 6.95–6.82 (5H, m) 2.73–2.67 (2H, m), 2.35–2.32 (2H, m), 1.53–1.43 (2H, m).

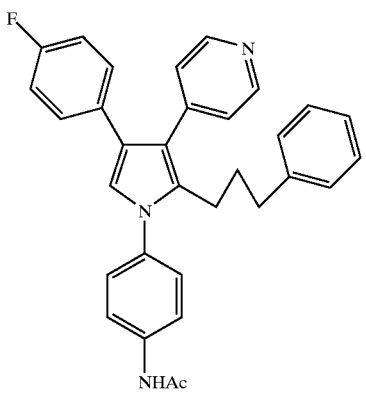

Compound 31

1-(4-Acetoaminophenyl)-4-(4-fluorophenyl)-2-(3-phenylpropyl)-3-(4-pyridyl)pyrrole Compound 32 (0.85 g, 0.0019 mol) was stirred for 16 hours in acetic anhydride (20 mL) and $H_2O$ (50 mL). The solution was extracted into ethyl acetate (100 mL), washed with $H_2O$ (3×50 mL), then washed with saturated sodium bicarbonate (3×50 mL) and then washed again with $H_2O$ (2×50 mL). The organics were dried over $Na_2SO_4$ and evaporated in vacuo to give Compound 31 (0.89 g, 96% yield) isolated as an oil. $^1$HNMR (CDCl$_3$) δ 8.41 (2H, d, J=5.6 Hz), 8.05 (1H, s), 7.73 (2H, d, J=8.6 Hz), 7.28 (2H, d, J=8.7 Hz), 7.17–7.04 (7H, m), 6.91–6.85 (4H, m), 6.79 (1H, s), 2.66–2.61 (2H, m), 2.35–2.30 (2H, m), 2.22 (3H, s), 1.59–1.51 (2H, m).

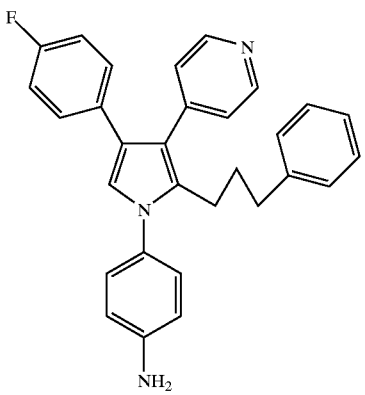

Compound 32

1-(4-Aminophenyl)-4-(4-fluorophenyl)-2-(3-phenylpropyl)-3-(4-pyridyl)pyrrole

Compound 30 (6.6 g, 0.0138 mol) was suspended in ethanol (200 mL) and ethyl acetate (50 mL) and exposed to reducing conditions for 16 hours on a Parr hydrogenator at 50 PSI. The mixture was filtered through Celite and evaporated in vacuo to give an oil. Trituration of this oil with acetonitrile and filtration of the resulting solid gave 3.2 g of Compound 32. The filtrate was evaporated in vacuo and purified on $SiO_2$ eluting with 50% ethyl acetate in hexane to give an additional 1.75 g of product. (combined yield 79%). $^1$HNMR (CDCl$_3$) δ 8.44 (2H, d, J=5.9 Hz), 7.22–6.71 (16H, m), 3.85 (2H, s), 2.63–2.57 (2H, m), 2.38–2.33 (2H, m), 1.61–1.49 (2H, m).

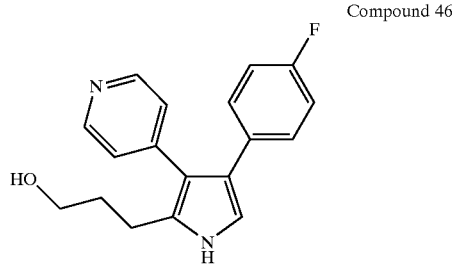

Compound 46

4-(4-Fluorophenyl)-2-(3-hydroxypropyl)-3-(4-pyridyl)pyrrole

A solution of 2-(3-benzyloxypropyl)-4-(4-fluorophenyl)-3-(4-pyridyl)pyrrole (0.95 g, 0.0025 mol) in ethanol (125 mL) containing concentrated HCl (0.2 mL) was added to Pd on carbon (0.2 g). This mixture was placed in a hydrogen atmosphere for 16 hours on a Parr hydrogenator at 50 PSI. The mixture was filtered through Celite and triethylamine (0.5 mL) was added to the resulting solution, followed by evaporation in vacuo to give a solid. The solid was extracted into ethyl acetate (100 mL) and washed with water (3×50 mL). The organics were dried over $Na_2SO_4$ and evaporated in vacuo to give a light yellow solid (0.7 g, 96% yield). $^1$HNMR (DMSO-d6) δ 11.10 (1H, s, NH), 8.44 (2H, d), 7.05 (6H, m), 6.91 (1H, d), 4.53 (1H, br s, OH), 3.49 (2H, br s), 2.64 (2H, t), 1.72 (2H, m).

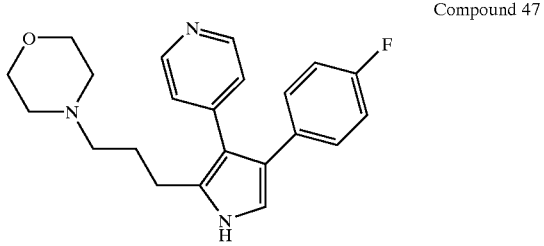

Compound 47

4-(4-Fluorophenyl)-2-(3-morpholinopropyl)-3-(4-pyridyl)pyrrole 4-(4-fluorophenyl)-2-(3-mesyloxypropyl)-3-(4-pyridyl) pyrrole (0.25 g, 0.0007 mol) was refluxed for 16 hours in $CH_2Cl_2$ (50 mL) and morpholine (0.25 mL). The solution was cooled and diluted with $CH_2Cl_2$ (~100 mL), then washed with $H_2O$ (3×50 mL). The organics were dried over $Na_2SO_4$ and evaporated in vacuo to give an oil. This oil was purified on $SiO_2$ eluting with 10% MeOH in $CH_2Cl_2$ to give 4-(4-fluorophenyl)-2-(3-morpholinopropyl)-3-(4-pyridyl) pyrrole isolated as a solid (0.088 g, 36% yield). $^1$HNMR (DMSO-d6) δ 11.12 (1H, s, NH), 8.42 (2H, d), 7.05 (6H, m), 6.95 (1H, d), 3.55 (4H, t), 2.62 (2H, t), 2.29 (6H, m), 1.71 (2H, m).

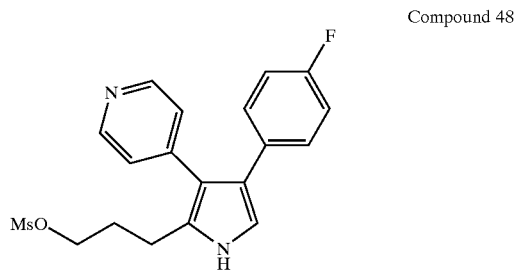

Compound 48

4-(4-Fluorophenyl)-2-(3-mesyloxypropyl)-3-(4-pyridyl)pyrrole 4-(4-fluorophenyl)-2-(3-hydroxypropyl)-3-(4-pyridyl) pyrrole (0.55 g, 0.0019 mol) was combined with triethylamine (0.52 mL, 0.0037 mol) in $CH_2Cl_2$ (50 mL) and cooled to 10° C. Methanesulfonylchloride (0.16 mL, 0.0020 mol) was added dropwise and the resulting mixture was allowed to warm to room temperature. This mixture was diluted with $CH_2Cl_2$ (50 mL) and washed with water (30 mL). The organics were dried over $Na_2SO_4$ and evaporated in vacuo to give an oil. This oil was dissolved in EtOAc and purified through a bed of $SiO_2$ (~20 mL) eluting with EtOAc. Evaporation of the solvent in vacuo gave a yellow solid (0.63 g, 91% yield). $^1$HNMR (DMSO-d6) δ 11.25 (1H, s, NH), 8.45 (2H, d), 7.09 (6H, m), 6.94 (1H, d), 4.19 (2H, t), 3.17 (3H, s), 2.71 (2H, t), 1.98 (2H, m).

III. Biological Assays and Activity
A. p38 Inhibition In-Vitro Enzyme Assay A solution (38 μL) of purified recombinant p38 (6xHis-p38 expressed in *E.coli*), myelin basic protein substrate (determined empirically), and a buffer of pH 7.5 (Hepes:25 mM, $MgCl_2$:10 mM, $MnCl_2$:10 mM) were added to 92 wells of a 96-well round bottom polypropylene plate. The amount of enzyme was determined empirically based on the linear range of the assay and the acceptable signal to noise ratio. The remaining wells were used for control ("CTRL") and background ("BKG"). The CTRL was prepared with the enzyme, substrate buffer and 2% DMSO, and the BKG was prepared with substrate buffer and 2% DMSO.

A solution (12 μL) of the test compound in DMSO was added to the testing wells. Compounds were diluted to 125 μM in 10% $DMSO/H_2O$ and assayed at 25 μM where the final DMSO concentration was 2%. The ATP/$^{33}$P-ATP solution (10 μL containing 50 μM unlabeled ATP and 1 μCi $^{33}$P-ATP) was added to all wells and the completed plates were mixed and incubated at 30° C. for 30 min. Ice-cold 50% TCA/10 mM sodium phosphate (60 μL) was added to each well and the plates were kept on ice for 15 min. The contents of each well were transferred to the wells of a 96-well filterplate (Millipore, MultiScreen-DP) and the filterplate was placed on a vacuum manifold fitted with a waste collection tray. The wells were washed five times with 10% TCA/10 mM sodium phosphate (200 μL) under vacuum. MicroScint-20 scintillant was added, and the plates were sealed using Topseal-S sheets and counted in a Packard TopCount scintillation counter using a $^{33}$P liquid program with color quench correction, where the output is in color quench-corrected cpm. The % inhibition of each test compound as shown in Table 2 was calculated by the following formula: % inhibition=[1−(sample−BKG)/(CTRL−BKG)]× 100.

TABLE 2

| Cpd. | R$_1$ | R$_2$ | R$_3$ | R$_4$ | % p38 inhib @ 10 μM |
|---|---|---|---|---|---|
| 2 | CH$_3$ | H | 4-pyr | 3,4-F—Ph | 15 |
| 3 | 4-NO$_2$—Ph | H | 4-pyr | 3,4-F—Ph | 80 |
| 4 | 4-CN—Ph | H | 4-pyr | 3,4-F—Ph | 21 |
| 14 | CH$_3$ | H | 4-pyr | 3-OCH$_3$—Ph | 43 |
| 18 | 4-CN—Ph | H | 4-pyr | 3-OCH$_3$—Ph | 23 |
| 28 | H | (CH$_2$)$_3$—Ph | 4-pyr | 4-F—Ph | 49 |
| 29 | CH$_3$ | H | 4-pyr | 4-F—Ph | 34 |
| 30 | 4-NO$_2$—Ph | H | 4-pyr | 4-F—Ph | 70 |
| 31 | 4-NO$_2$—Ph | (CH$_2$)$_3$—Ph | 4-pyr | 4-F—Ph | 67 |
| 32 | 4-NHAc—Ph | (CH$_2$)$_3$—Ph | 4-pyr | 4-F—Ph | 38 |
| 33 | 4-NH$_2$—Ph | (CH$_2$)$_3$—Ph | 4-pyr | 4-F—Ph | 51 |

Although compounds were initially tested at 20 μM, when warranted, the compounds were also tested at 4-fold increments above and below that concentration. In addition, the IC$_{50}$ was calculated for some compounds using the Deltagraph 4-parameter curve-fitting program.

B. In-Vitro Whole Cell Assay for TNF-α Inhibition

Freshly obtained venous blood was anticoagulated with heparin, diluted with an equal volume of phosphate buffered saline ("PBS") and placed in a sterile tube or other container. Aliquots (30 mL) of this mixture were transferred to centrifuge tubes which were underlaid with Ficoll-Hypaque (15 mL). The prepared tubes were centrifuged at 400×g, without braking, for 30 min at room temperature. Approximately ½ to ⅔ of the platelet layer above the mononuclear cell band was removed with a pipette. The majority of the mononuclear cell layer was carefully removed using a pipette and these PBMC's were diluted with PBS and spun at 600×g for 15 min. The resulting PBMC's were washed with another portion of PBS and spun at 400×g for 10 min at room temperature. The recovered pellets were diluted in low endotoxin RPMI/1% FCS culture medium, and gave a cell concentration of 0.5–2.0×10$^6$ PMBC/mL. A small volume of the suspension was removed for counting on a hemocytometer and the remaining preparation was centrifuged at 200×g for 15 min at room temperature. The recovered pelleted PMBC's were resuspended in RPMI/1% FCS to a concentration of 1.67×10$^6$/mL.

To run the assay, the PBMC suspension (180 μL) was transferred to duplicate wells of a 96-well flat-bottom microtiter plate and incubated for 1 h at 37° C. A solution of test compound (10 μL: prepared at 20× the desired final concentration) was added to each well and the plate was incubated for 1 h at 37° C. A solution (10 μL) of LPS in RPMI/1% FCS (200 ng/mL) was added and the wells were incubated overnight at 37° C. The supernate (100 μL) was removed from each well and diluted with RPMI/1% FCS (400 μL). The samples were analyzed for TNF-α using a commercial ELISA kit (Genzyme).

Select compounds of the invention are listed in Table 3. The compounds were tested for their ability to inhibit TNF-α production. The IC50 nM results are listed for the indicated compounds.

TABLE 3

| Cpd. | R$_1$ | R$_2$ | R$_3$ | R$_4$ | TNF-α IC$_{50}$ nM | Scheme |
|---|---|---|---|---|---|---|
| 1 | H | H | 4-pyr | 3,4-F—Ph | 20 | 2 |
| 2 | CH$_3$ | H | 4-pyr | 3,4-F—Ph | 30 | 1 |
| 3 | 4-NO$_2$—Ph | H | 4-pyr | 3,4-F—Ph | 2 | 4 |
| 4 | 4-CN—Ph | H | 4-pyr | 3,4-F—Ph | 2 | 4 |
| 5 | 4-CH$_3$SO$_2$—Ph | H | 4-pyr | 3,4-F—Ph | 30 | 4 |
| 6 | CH$_3$ | H | 4-pyr | 3,5-F—Ph | 175 | 1 |
| 7 | CH$_3$ | H | 4-pyr | 3-CF$_3$, 4-F—Ph | 100 | 1 |
| 8 | CH$_3$ | H | 4-pyr | 3-CF$_3$, 5-F—Ph | 1500 | 1 |
| 9 | CH$_3$ | H | 4-pyr | 3-CF$_3$—Ph | 125 | 1 |
| 10 | CH$_3$ | H | 4-pyr | 3-F—Ph | 125 | 1 |
| 11 | CH$_3$ | H | 4-pyr | 3-NO$_2$—Ph | 100 | 1 |
| 12 | H | H | 4-pyr | 3-OH—Ph | 300 | 2 |
| 13 | H | H | 4-pyr | 3-OCH$_3$—Ph | 55 | 2 |
| 14 | CH$_3$ | H | 4-pyr | 3-OCH$_3$—Ph | 55 | 1 |
| 15 | 4-NO$_2$—Ph | H | 4-pyr | 3-OCH$_3$—Ph | 20 | 4 |
| 16 | 4-NHAc—Ph | H | 4-pyr | 3-OCH$_3$—Ph | 75 | 4 |
| 17 | 4-NH$_2$—Ph | H | 4-pyr | 3-OCH$_3$—Ph | 95 | 4 |
| 18 | 4-CN—Ph | H | 4-pyr | 3-OCH$_3$—Ph | 15 | 4 |
| 19 | 4-CH$_3$SO$_2$—Ph | H | 4-pyr | 3-OCH$_3$—Ph | 30 | 4 |
| 20 | 2-pyr | H | 4-pyr | 3-OCH$_3$—Ph | 150 | 4 |
| 21 | 2,4-NO$_2$—Ph | H | 4-pyr | 3-OCH$_3$—Ph | 80 | 4 |
| 22 | 4-SO$_2$—Ph | H | 4-pyr | 3-OCH$_3$—Ph | 1000 | 4 |
| 23 | (CH$_2$)$_3$—Ph | H | 4-pyr | 3-OCH$_3$—Ph | 2000 | 4 |
| 24 | H | H | 4-pyrimidine | 3-OCH$_3$—Ph | 250 | 2 |
| 25 | CH$_3$ | H | 4-pyr | 3-thienyl | 900 | 1 |
| 26 | CH$_3$ | H | 4-pyr | 4-OCH$_3$—Ph | 2000 | 1 |
| 27 | H | H | 4-pyr | 4-F—Ph | 90 | 2 |
| 28 | H | (CH$_2$)$_3$—Ph | 4-pyr | 4-F—Ph | 3.5 | 3 |
| 29 | CH$_3$ | H | 4-pyr | 4-F—Ph | 200 | 1 |
| 30 | 4-NO$_2$—Ph | H | 4-pyr | 4-F—Ph | 2 | 4 |
| 31 | 4-NO$_2$—Ph | (CH$_2$)$_3$—Ph | 4-pyr | 4-F—Ph | 15 | 4 |
| 32 | 4-NHAc—Ph | (CH$_2$)$_3$—Ph | 4-pyr | 4-F—Ph | 5 | 5 |
| 33 | 4-NH$_2$—Ph | (CH$_2$)$_3$—Ph | 4-pyr | 4-F—Ph | 8 | 5 |
| 34 | CH$_3$ | H | 4-pyr | 4-pyr | 3000 | 1 |
| 35 | CH$_3$ | H | 4-pyr | 4-SCH$_3$—Ph | 250 | 1 |
| 36 | CH$_3$ | H | 4-pyr | 4-(CH$_3$)$_2$N—Ph | 500 | 1 |
| 37 | CH$_3$ | H | 4-pyr | 4-SOCH$_3$—Ph | 3000 | 1 |
| 38 | CH$_3$ | H | 4-pyr | Ph | 350 | 1 |
| 39 | (CH$_2$)$_3$N(CH$_2$)$_5$ | (CH$_2$)$_3$—Ph | 4-pyr | 4-F—Ph | 5 | 4 |
| 40 | (CH$_2$)$_2$N(CH$_2$)$_5$ | (CH$_2$)$_3$—Ph | 4-pyr | 4-F—Ph | 3 | 4 |
| 41 | (CH$_2$)$_2$CH(CH$_2$)$_3$NCH$_3$ | (CH$_2$)$_3$—Ph | 4-pyr | 4-F—Ph | 5 | 4 |
| 42 | (CH$_2$)$_2$CH(CH$_2$)$_3$NCH$_3$CH$_2$ | (CH$_2$)$_3$—Ph | 4-pyr | 4-F—Ph | 2 | 4 |
| 43 | (CH$_2$)$_2$N(CH$_2$)$_2$O(CH$_2$)$_2$ | (CH$_2$)$_3$—Ph | 4-pyr | 4-F—Ph | 1 | 4 |
| 44 | (CH$_2$)$_3$N(CH$_3$)$_2$ | (CH$_2$)$_3$—Ph | 4-pyr | 4-F—Ph | 8 | 4 |
| 45 | (CH$_2$)$_2$N(CH$_2$)$_4$ | (CH$_2$)$_3$—Ph | 4-pyr | 4-F—Ph | 3 | 4 |
| 46 | H | (CH$_2$)$_3$—OH | 4-pyr | 4-F—Ph | 544 | 6 |
| 47 | H | (CH$_2$)$_2$N(CH$_2$)$_2$O(CH$_2$)$_2$ | 4-pyr | 4-F—Ph | 177 | 6 |

C. In Vivo Rodent Assay for Inhibition of TNF-α Production

The ability of the instant compounds to inhibit LPS-induced TNF-α production was demonstrated in the following in vivo rodent assays. Mice (BALB/cJ females, Jackson Laboratories) or rats (Lewis males, Charles River) were fasted for 30 min prior to oral dosing with 5–10 mL/kg of test compound at 5–50 mg/kg. Thirty minutes after dosing, the animals were injected intraperitoneally with LPS at 1 mg/kg and returned to their cages for 1 h. Animals were anesthetized by $CO_2$, exsanguinated by cardiac puncture and whole blood collected (0.1–0.7 mL). The blood was allowed to clot and serum was transferred to a centrifuge tube. This sample was centrifuged, and serum was collected, aliquoted and frozen at −80° C. Samples were tested by commercial ELISA's for TNF-α (Endogen for mouse TNF-α and Biosource for rat TNF-α). The in vivo test results for select compounds of the invention are listed in Table 4. The compounds were tested for their ability to inhibit TNF-α production in mice and the data are listed as % inhibition at 25 mg/kg.

TABLE 4

| Cpd. | R1 | R2 | R3 | R4 | TNF-α % Inhibition Mouse |
|---|---|---|---|---|---|
| 1 | H | H | 4-pyr | 3,4-F—Ph | 96 |
| 7 | $CH_3$ | H | 4-pyr | 3-$CF_3$, 4-F—Ph | 79 |
| 11 | $CH_3$ | H | 4-pyr | 3-$NO_2$—Ph | 94 |
| 14 | $CH_3$ | H | 4-pyr | 3-$OCH_3$—Ph | 71 |
| 16 | 4-NHAc—Ph | H | 4-pyr | 3-$OCH_3$—Ph | 50 |
| 17 | 4-$NH_2$—Ph | H | 4-pyr | 3-$OCH_3$—Ph | 66 |
| 18 | 4-CN—Ph | H | 4-pyr | 3-$OCH_3$—Ph | 60 |
| 19 | 4-$CH_3SO_2$—Ph | H | 4-pyr | 3-$OCH_3$—Ph | −127 |
| 27 | H | H | 4-pyr | 4-F—Ph | 100 |
| 28 | H | $(CH_2)_3$—Ph | 4-pyr | 4-F—Ph | 10 |
| 30 | 4-$NO_2$—Ph | H | 4-pyr | 4-F—Ph | 53 |
| 39 | $(CH_2)_3N(CH_2)_5$ | $(CH_2)_3$—Ph | 4-pyr | 4-F—Ph | 100 |
| 40 | $(CH_2)_2N(CH_2)_5$ | $(CH_2)_3$—Ph | 4-pyr | 4-F—Ph | 96 |
| 41 | $(CH_2)_2CH(CH_2)_3NCH_3$ | $(CH_2)_3$—Ph | 4-pyr | 4-F—Ph | 100 |
| 42 | $(CH_2)_2CH(CH_2)_3NCH_3CH_2$ | $(CH_2)_3$—Ph | 4-pyr | 4-F—Ph | 100 |
| 43 | $(CH_2)_2N(CH_2)_2O(CH_2)_2$ | $(CH_2)_3$—Ph | 4-pyr | 4-F—Ph | 93 |
| 44 | $(CH_2)_3N(CH_3)_2$ | $(CH_2)_3$—Ph | 4-pyr | 4-F—Ph | 100 |
| 45 | $(CH_2)_2N(CH_2)_4$ | $(CH_2)_3$—Ph | 4-pyr | 4-F—Ph | 99 |
| 47 | H | $(CH_2)_2N(CH_2)_2O(CH_2)_2$ | 4-pyr | 4-F—Ph | 77 |

The in vivo test results for select compounds of the invention are listed in Table 5. The compounds were tested for their ability to inhibit TNF-α production in mice and the data are listed as % inhibition at 10 mg/kg.

TABLE 5

| Cpd. | R1 | R2 | R3 | R4 | TNF-α % Inhibition Mouse |
|---|---|---|---|---|---|
| 3 | 4-$NO_2$—Ph | H | 4-pyr | 3,4-F—Ph | 81 |
| 7 | $CH_3$ | H | 4-pyr | 3-$CF_3$, 4-F—Ph | 61 |
| 11 | $CH_3$ | H | 4-pyr | 3-$NO_2$—Ph | 74 |
| 14 | $CH_3$ | H | 4-pyr | 3-$OCH_3$—Ph | 41 |
| 18 | 4-CN—Ph | H | 4-pyr | 3-$OCH_3$—Ph | 24 |
| 27 | H | H | 4-pyr | 4-F—Ph | 73 |
| 28 | H | $(CH_2)_3$—Ph | 4-pyr | 4-F—Ph | 10 |
| 31 | 4-$NO_2$—Ph | $(CH_2)_3$—Ph | 4-pyr | 4-F—Ph | 47 |

TABLE 5-continued

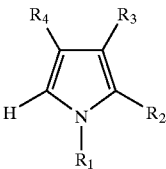

| Cpd. | R1 | R2 | R3 | R4 | TNF-α % Inhibition Mouse |
|---|---|---|---|---|---|
| 32 | 4-NHAc—Ph | $(CH_2)_3$—Ph | 4-pyr | 4-F—Ph | 48 |
| 39 | $(CH_2)_3N(CH_2)_5$ | $(CH_2)_3$—Ph | 4-pyr | 4-F—Ph | 36 |
| 40 | $(CH_2)_2N(CH_2)_5$ | $(CH_2)_3$—Ph | 4-pyr | 4-F—Ph | 96 |
| 41 | $(CH_2)_2CH(CH_2)_3NCH_3$ | $(CH_2)_3$—Ph | 4-pyr | 4-F—Ph | 100 |
| 42 | $(CH_2)_2CH(CH_2)_3NCH_3CH_2$ | $(CH_2)_3$—Ph | 4-pyr | 4-F—Ph | 100 |
| 43 | $(CH_2)_2N(CH_2)_2O(CH_2)_2$ | $(CH_2)_3$—Ph | 4-pyr | 4-F—Ph | 93 |
| 44 | $(CH_2)_3N(CH_3)_2$ | $(CH_2)_3$—Ph | 4-pyr | 4-F—Ph | 100 |
| 45 | $(CH_2)_2N(CH_2)_4$ | $(CH_2)_3$—Ph | 4-pyr | 4-F—Ph | 99 |

References

1. C. Dinarello, et al., Inflammatory Cytokines: Interleukin-1 and Tumor Necrosis Factor as Effector Molecules in Autoimmune Diseases, *Curr. Opin. Immunol.* 1991, 3, 941–48.
2. M. J. Elliot, et al., Treatment of Rheumatoid Arthritis with Chimeric Monoclonal Antibodies to Tumor Necrosis Factor α, *Arthritis Rheum.* 1993, 36, 1681–90.
3. J. C. Boehm, et al., 1-Substituted 4-Aryl-5-pyridinylimidazoles: A New Class of Cytokine Suppressive Drugs with Low 5-Lipoxygenase and Cyclooxygenase Inhibitory Potency, *J. Med. Chem.*, 1996, 39, 3929–37.
4. International Publication No. WO 93/14081.
5. A. M. Badger, et al., Pharmacological Profile of SB 203580, A Selective Inhibitor of Cytokine Suppressive Binding Protein p38 Kinase, in Animal Models of Arthritis, Bone Resorption, Endotoxin Shock and Immune Function, *The Journal of Pharmacology and Experimental Therapeutics*, 1996, 279, 1453–61.
6. D. Griswold, et al., Pharmacology of Cytokine Suppressive Anti-Inflammatory Drug Binding Protein (CSBP), A Novel Stress-induced Kinase, *Pharmacology Communications*, 1996, 7, 323–29.
7. U.S. Pat. No. 5,776,954.
8. International Publication No. WO 97/05877.
9. International Publication No. WO 97/05878.
10. Davis, Roger J., et al., Opposing effects of ERK and JNK-p38 MAP Kinases on Apoptosis, *Science*, 1995, 270(5240), 1326–31.
11. Heidenreich, Kim A., et al., Inhibition of p38 Mitogen-Activated Protein Kinase by Insulin in Cultured Fetal Neurons, *J. Biol. Chem.*, 1996, 271(17), 9891–4.
12. Arvanitakis, L., et al., G-Protein-Coupled Receptor of Kaposi's Sarcoma-Associated Herpesvirus is a Viral Oncogene and Angiogenesis Activator, *Nature*, 1998, 391(6662), 86–89.
13. Pitha, Paula M., et al., Early Activation of Mitogen-Activated Protein Kinase Kinase, Extracellular Signal-Regulated Kinase, p38 Mitogen-Activated Protein Kinase, and c-Jun N-terminal Kinase in Response to Binding of Simian Immunodeficiency Virus to Jurkat T Cells Expressing CCR5 Receptor, *Virology*, 1998, 252(1), 210–217.
14. Bukrinsky, M., The Critical Role of p38 MAP Kinase in T Cell HIV-1 Replication, *Mol. Med.*, 1997, 3(5), 339–346.

What is claimed is:

1. A compound of the following structure:

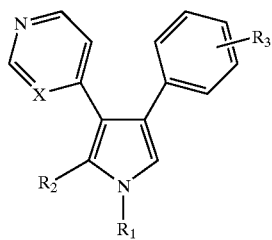

or a pharmaceutically acceptable salt thereof, wherein:
(a) $R_1$ is selected from the group consisting of (i) hydrogen, (ii) $C_{1-5}$alkyl, (iii) substituted or unsubstituted $C_{1-5}$alkylamino, (iv) N-containing $C_{1-5}$alkyl heterocycle selected from thiazolidine, piperidine, morpholine, piperazine, thiomorpholine, pyrrolidine, thiazine, pyrrole and imidazole, (v) phenyl, (vi) phenyl independently substituted with one or more of $C_{1-5}$alkyl, amino, substituted amino, nitro, nitrile and sulfone, and (vii) pyridine;
(b) $R_2$ is selected from the group consisting of (i) hydrogen, (ii) $(CH_2)_3OH$, (iii) substituted or unsubstituted $C_{1-5}$alkyl phenyl, and (iv) N-containing $C_{1-5}$alkyl heterocycle selected from thiazolidine, piperidine, morpholine, piperazine, thiomorpholine, pyrrolidine, thiazine, pyrrole and imidazole;
(c) $R_3$ is one or more substituents independently selected from the group consisting of hydrogen, halogen, methoxy, nitro, trifluoromethyl, hydroxy, dimethylamino and methylsulfoxide; and
(d) X is C.

2. The compound of claim 1, wherein:
(a) $R_1$ is selected from the group consisting of (i) hydrogen, (ii) $C_{1-5}$alkyl, (iii) substituted or unsubstituted $C_{1-5}$alkylamino, (iv) N-containing $C_{1-5}$alkyl heterocycle selected from piperidine, morpholine and pyrrolidine, and (v) phenyl substituted with a substituent selected from the group consisting of amino, substituted amino, nitro and nitrile;
(b) $R_2$ is selected from the group consisting of hydrogen and $(CH_2)_3$phenyl;

(c) R₃ is selected from the group consisting of halogen, nitro and trifluoromethyl; and
(d) X is C.

3. The compound according to claim 1 of the structure:

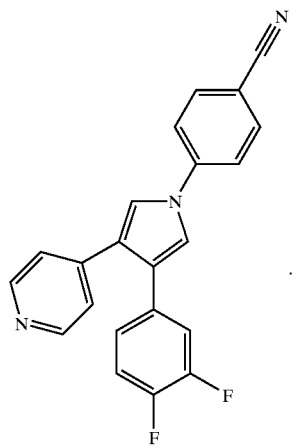

4. The compound according to claim 1 of the structure:

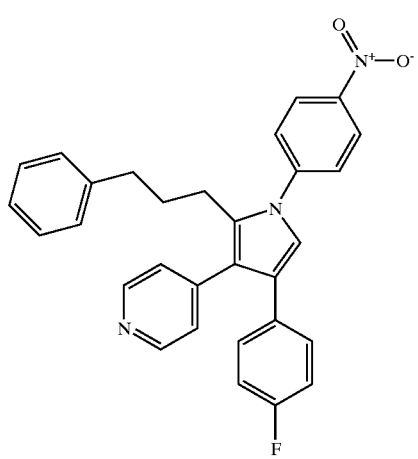

5. The compound according to claim 1 of the structure:

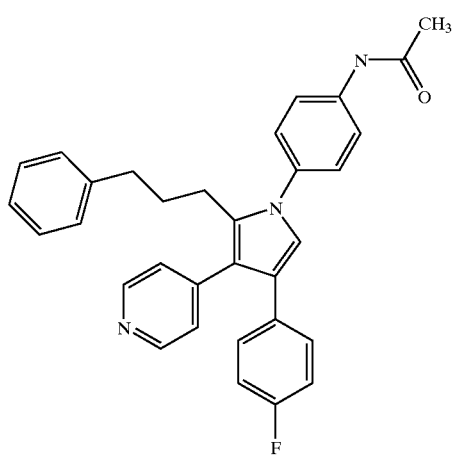

6. The compound according to claim 1 of the structure:

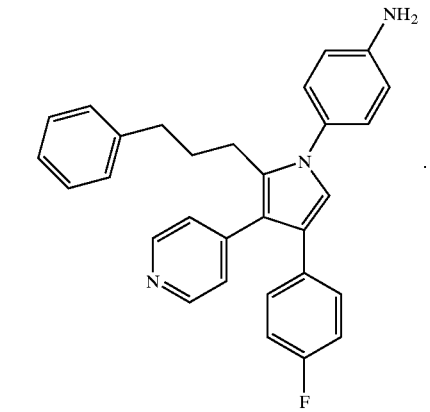

7. The compound according to claim 1 of the structure:

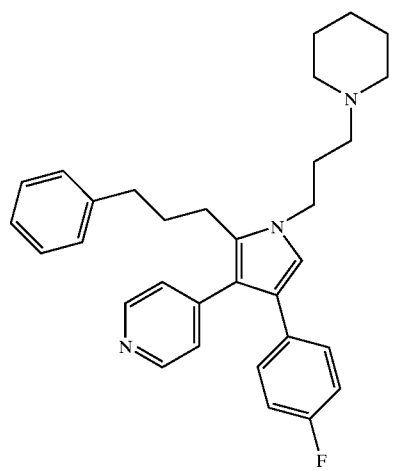

8. The compound according to claim 1 of the structure:

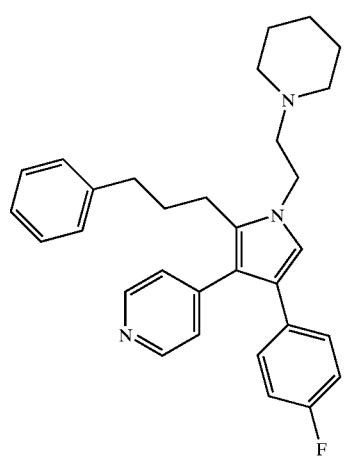

9. The compound according to claim 1 of the structure:
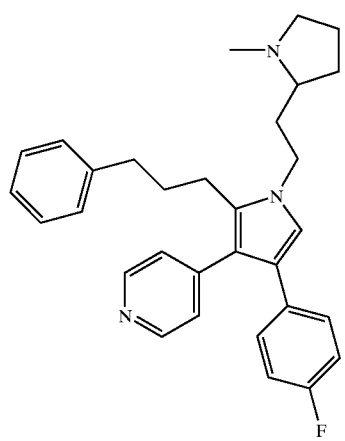
10. The compound according to claim 1 of the structure:
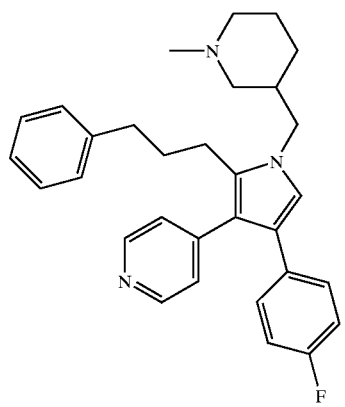
11. The compound according to claim 1 of the structure:
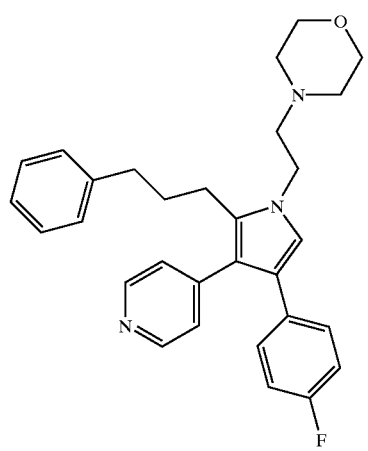
12. The compound according to claim 1 of the structure:
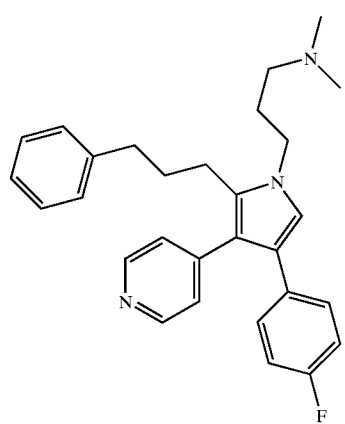
13. The compound according to claim 1 of the structure:
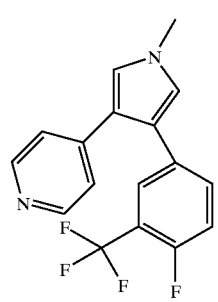
14. The compound according to claim 1 of the structure:

15. The compound according to claim 1 of the structure:

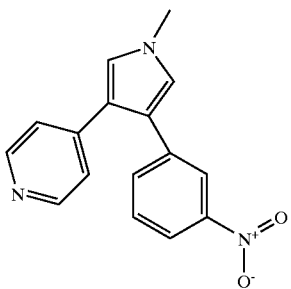

16. The compound according to claim 1 of the structure:

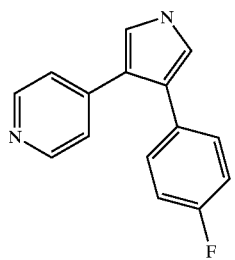

17. The compound according to claim 1 of the structure:

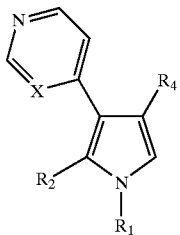

or a pharmaceutically acceptable salt thereof, wherein:

(a) $R_1$ is selected from the group consisting of (i) hydrogen, (ii) $C_{1-5}$alkyl, (iii) substituted or unsubstituted $C_{1-5}$alkylamino, (iv) N-containing $C_{1-5}$alkyl heterocycle selected from thiazolidine, piperidine, morpholine, piperazine, thiomorpholine, pyrrolidine, thiazine, pyrrole and imidazole, (v) phenyl, (vi) phenyl independently substituted with one or more of $C_{1-5}$alkyl, amino, substituted amino, nitro, nitrile and sulfone, and (vii) pyridine;

(b) $R_2$ is selected from the group consisting of (i) hydrogen, (ii) $(CH_2)_3OH$, (iii) substituted or unsubstituted $C_{1-5}$alkyl phenyl, and (iv) N-containing $C_{1-5}$alkyl heterocycle selected from thiazolidine, piperidine, morpholine, piperazine, thiomorpholine, pyrrolidine, thiazine, pyrrole and imidazole;

(c) $R_4$ is a substituted or unsubstituted heterocycle selected from pyridine, pyrimidine, furan or thiophene; and, (d) X is C.

18. The compound of claim 17, wherein:

(a) $R_1$ is selected from the group consisting of (i) $C_{1-5}$alkyl, (ii) substituted or unsubstituted $C_{1-5}$alkylamino, (iii) substituted or unsubstituted $C_{1-5}$alkyl heterocyclic amino, (iv) phenyl, and (v) phenyl independently substituted with one or more of amino, substituted amino, nitro or nitrile;

(b) $R_2$ is selected from the group consisting of hydrogen and $(CH_2)_3$phenyl; and (c) X is C.

19. A pharmaceutical composition comprising the compound of claim 1 or claim 17 and a pharmaceutically acceptable carrier.

\* \* \* \* \*